(12) United States Patent
Lange et al.

(10) Patent No.: US 10,583,076 B2
(45) Date of Patent: Mar. 10, 2020

(54) AGENT AND METHOD FOR THE TEMPORARY DEFORMATION OF KERATIN-CONTAINING FIBERS

(71) Applicant: Henkel AG & Co. KGaA, Duesseldorf (DE)

(72) Inventors: Julia Bibiane Lange, Bad Bramstedt (DE); Diane Metten, Hamburg (DE); Cyrielle Martinez, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/140,685

(22) Filed: Sep. 25, 2018

(65) Prior Publication Data
US 2019/0099350 A1    Apr. 4, 2019

(30) Foreign Application Priority Data
Sep. 29, 2017   (DE) .................. 10 2017 217 456

(51) Int. Cl.
*A61K 8/81* (2006.01)
*A61Q 5/06* (2006.01)

(52) U.S. Cl.
CPC .......... *A61K 8/8147* (2013.01); *A61K 8/8117* (2013.01); *A61K 8/8152* (2013.01); *A61K 8/8176* (2013.01); *A61K 8/8182* (2013.01); *A61Q 5/06* (2013.01); *A61K 2800/594* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 2004/0115234 A1* | 6/2004 | Gewirtz | A61K 8/37 424/401 |
| 2015/0079015 A1* | 3/2015 | Bolognini | A61K 8/8152 424/70.7 |
| 2016/0008245 A1* | 1/2016 | Durkee | A61K 8/40 424/60 |

FOREIGN PATENT DOCUMENTS

| | | |
|---|---|---|
| EP | 3069709 A1 | 9/2016 |
| WO | 0154660 A1 | 8/2001 |
| WO | 2012168035 A1 | 12/2012 |
| WO | 2014192780 A1 | 12/2014 |
| WO | 2015039826 A1 | 3/2015 |

OTHER PUBLICATIONS

Eggar & Co (Chemicals) Limited, "Hair Gel Formulation", Research Disclosure, vol. 503, No. 18, 2006.

* cited by examiner

*Primary Examiner* — Jeffrey T. Palenik
(74) *Attorney, Agent, or Firm* — Lorenz & Kopf, LLP

(57) ABSTRACT

Cosmetic compositions for the temporarily shaping of keratinic fibers and methods for using such cosmetic compositions are provided. In one example, a cosmetic composition includes at least one non-crosslinked, hydrophobically modified (meth)acrylic acid copolymer, and at least one copolymer that includes at least in part monomer units. The monomer units include styrene, and acrylic acid and/or methacrylic acid.

13 Claims, No Drawings

AGENT AND METHOD FOR THE TEMPORARY DEFORMATION OF KERATIN-CONTAINING FIBERS

CROSS-REFERENCE TO RELATED APPLICATION

This application claims priority to German Patent Application No. 10 2017 217 456.0, filed Sep. 29, 2017, which is incorporated herein by reference in its entirety.

TECHNICAL FIELD

The present disclosure relates to a cosmetic composition based on two specific anionic copolymers for hair setting or for the temporary shaping of keratinic fibers, in particular human hair, and method and use of this composition and its use for improving long-term holding and moisture resistance.

BACKGROUND

The temporary design of hairstyles for a longer period up to several days usually requires the application of setting active ingredients. Hair treatment agents which are used for temporary shaping of the hair therefore play an important role. Corresponding agents for temporary deformation usually contain synthetic polymers and/or waxes as the setting active ingredient. Agents for supporting the temporary shaping of keratin-containing fibers can be formulated, for example, as a hair spray, hair wax, hair gel or hair mousse.

The most important property of an agent for the temporary deformation of hair, hereinafter also referred to as a styling agent, is to give the treated fibers in the newly modeled shape, i.e., a shape impressed on the hair, the strongest possible hold. One also speaks of strong hairstyle hold or the high degree of hold of the styling agent. The hairstyle hold is essentially determined by the type and amount of the setting active ingredients used, wherein, however, an influence of the other ingredients of the styling agent may also be given.

In addition to a high degree of hold, styling agents must meet a whole series of other requirements. These may be broadly subdivided into properties on the hair, properties of the particular formulation, e.g., properties of the foam, of the gel or of the sprayed aerosol, and of properties which affect the handling of the styling agent, wherein the properties on the hair are of particular importance. Particularly noteworthy are moisture resistance, low tack and a balanced conditioning effect. Furthermore, a styling agent should be universally applicable for all hair types and mild to hair and skin.

A variety of synthetic polymers which are used in styling agents have already been developed as setting active ingredients to meet the different requirements. The polymers can be subdivided into cationic, anionic, nonionic and amphoteric setting polymers.

European Patent Application EP 3 069 709 A1 describes hair cosmetic polymer mixtures which contain, in addition to an oxyalkylene polymer, the hydrophobically modified (meth)acrylic acid copolymer having the trade name Luvigel Fit (INCI: Acrylates (C10-30) Alkyl Methacrylate Copolymer).

Hair fixing agents based on copolymers of styrene with (meth)acrylic acid and/or their esters are described in the international patent application WO2012/168035 A1.

Ideally, when applied to hair, the polymers provide a polymer film which, on the one hand, gives the hairstyle a strong hold but, on the other hand, is sufficiently flexible not to break under stress. If the polymer film is too brittle, it results in the formation of so-called film plaques, that is, residues that detach during the movement of the hair and give the impression that the user of the corresponding styling agent might have dandruff. Similar problems arise when waxes are used as a setting active ingredient in the styling agent. If the styling agent is a gel or a paste, the polymers should also have thickening properties.

BRIEF SUMMARY

Cosmetic compositions for the temporarily shaping of keratinic fibers and methods for using such cosmetic compositions are provided herein. In an exemplary embodiment, a cosmetic composition for the temporarily shaping of keratinic fibers comprises at least one non-crosslinked, hydrophobically modified (meth)acrylic acid copolymer, and at least one copolymer that comprises at least in part monomer units. The monomer units include styrene, and acrylic acid and/or methacrylic acid.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

An object of the present disclosure was to provide further suitable polymer combinations which are distinguished by good film-forming and/or setting properties, have a very high degree of hold, without having to relinquish flexibility and good moisture resistance, in particular perspiration and water resistance, and also be suitable for the production of stable viscous and stable transparent cosmetic compositions. In particular, currently available styling agents can still be improved to the extent that a good combination of stiffness and long-term holding (high humidity curl retention) is not always sufficiently guaranteed. It is therefore an object of the present disclosure to provide such styling agents which, in addition to the abovementioned properties, in particular provide both good stiffness and good long-term holding.

This was achieved as contemplated herein by a combination of two specific anionic copolymers.

The present disclosure provides:

A cosmetic composition for the temporary shaping of keratinic fibers, including:
  a) at least one non-crosslinked, hydrophobically modified (meth)acrylic acid copolymer, and
  b) at least one copolymer which is composed of at least the following monomer units:
    styrene
    acrylic acid and/or methacrylic acid.

Cosmetic composition according to the foregoing point, wherein the proportion by weight of the copolymer a) in the total weight of the composition is from about 0.1 to about 15% by weight, preferably from about 0.2 to about 10% by weight and in particular from about 0.5 to about 7.0% by weight.

Cosmetic composition according to one of the preceding points, wherein the copolymer a) is obtained by conversion of:

at least one monomer (a1) from the group of acrylic acid, methacrylic acid, $C_1$-$C_6$ alkyl acrylic acid ester, $C_1$-$C_6$ alkyl methacrylic acid ester, with at least one monomer (a2) from the group of $C_{10}$-30 alkyl acrylates, $C_{10}$-30 alkyl methacrylates, $C_{10\text{-}30}$ alkyl PEG acrylates, $C_{10\text{-}30}$ alkyl PEG methacrylates or $C_{10\text{-}30}$ alkyl PEG itaconates.

Cosmetic composition according to one of the preceding points, wherein the copolymer a) is obtained by conversion of:

at least one monomer (a1) from the group of acrylic acid, methacrylic acid, with at least one monomer (a2) from the group of $C_{10\text{-}30}$ alkyl methacrylates.

Cosmetic composition according to one of the preceding points, wherein the copolymer a) is selected from the group of compounds having the INCI name Acrylates/$C_{10\text{-}30}$-Alkyl Methacrylate Copolymer.

Cosmetic composition according to one of the preceding points, wherein the proportion by weight of the copolymer b) in the total weight of the composition is from about 0.1 to about 10% by weight, preferably from about 0.2 to about 8.0% by weight and in particular from about 0.5 to about 7.0% by weight.

Cosmetic composition according to one of the preceding points, wherein the copolymer b) based on its total weight of at least about 90% by weight, preferably at least about 95% by weight and in particular at least about 97% by weight of the monomers styrene acrylic acid and/or methacrylic acid.

Cosmetic composition according to one of the preceding points, wherein the copolymer b) based on its total weight of at least about 90% by weight, preferably at least about 95% by weight and in particular at least about 97% by weight of the monomers styrene acrylic acid and/or methacrylic acid acrylic acid esters and/or methacrylic acid esters.

Cosmetic composition according to one of the preceding points, wherein the copolymer b) is selected from the group of compounds having the INCI name Styrene/Acrylates Copolymer.

Cosmetic composition according to one of the preceding points, wherein the weight ratio of copolymer a) to copolymer b) is from about 10:1 to about 1:10, preferably from about 5:1 to about 1:5 and in particular from about 3:1 to about 1:3.

Cosmetic composition according to one of the preceding points, exemplified in that it further includes:

c) polyvinylpyrrolidone and/or vinylpyrrolidone/vinyl acetate copolymer, preferably polyvinylpyrrolidone.

Cosmetic composition according to the foregoing point, wherein the proportion by weight of the polyvinylpyrrolidone and/or vinylpyrrolidone/vinyl acetate copolymer c) in the total weight of the cosmetic composition is from about 0.1 to about 10% by weight, preferably from about 2.0 to about 8.5% by weight and in particular from about 3.0 to about 7.0% by weight.

Cosmetic composition according to one of the preceding points, wherein the composition, based on its total weight, contains from about 0.05 to about 2.0% by weight, preferably from about 0.1 to about 1.0% by weight and in particular from about 0.1 to about 0.5% by weight of an aminoalcohol, preferably 2-amino-2-methylpropanol.

Cosmetic composition according to one of the preceding points, wherein the composition includes, based on its total weight, at least about 20% by weight, preferably at least about 40% by weight and in particular at least about 70% by weight of water and ethanol.

Cosmetic composition according to one of the preceding points, exemplified in that the composition is in the form of a hair gel, hair spray, hair mousse or hair wax.

Use of a cosmetic composition according to any one of the preceding points for the temporary deformation of keratin-containing fibers, in particular human hair.

Use of a cosmetic composition according to any one of the preceding points for improving the holding of temporarily deformed keratinic fibers.

Use of a cosmetic composition according to any one of the preceding points for improving the moisture resistance of temporarily deformed keratinic fibers.

Method for the temporary deformation of keratin-containing fibers, in particular human hair, in which the keratinic fibers are acted upon by a cosmetic composition according to one of the preceding points and temporarily fixed in their shape.

In the context of the present disclosure, it has surprisingly been determined that an improved hold of styling products can be achieved by combining known two components which are already used in styling products. Other commonly required properties of styling products such as moisture resistance, stiffness and low tack remained unchanged. Such a good combination of properties was not expected even with knowledge of the individual components and was surprising. It was shown experimentally that the combination of the two components resulted in a strongly superadditive, i.e., synergistic effect with respect to hold, which was manifested by the HHRC test (High Humidity Curl Retention Test).

The term keratinic fibers as contemplated herein comprises furs, wool and feathers, but in particular human hair.

The essential components of the cosmetic composition are the non-crosslinked, hypodrophobically modified copolymer a) and the anionic copolymer b) different from the copolymer a).

In addition to the abovementioned advantages, the cosmetic compositions are distinguished with respect to alternative cosmetic agents, in particular, by improved long-term holding. As for the cosmetic properties of the compositions as contemplated herein, a weight ratio of the polymers a) and b) in the cosmetic composition from about 10:1 to about 1:10, preferably from about 5:1 to about 1:5 and in particular from about 3:1 to about 1:3 has proven to be particularly advantageous, for example, for the moisture resistance and low tack.

As a first required component, the cosmetic compositions contain a non-crosslinked, hydrophobically modified (meth)acrylic acid copolymer which is composed of at least two different structural units. In addition, further structural units may be present.

Copolymers are preferably used as hydrophobically modified (meth)acrylic acid copolymers a), which can be traced back to at least one monomer (a1) from the group of unsaturated carboxylic acids and unsaturated carboxylic esters, and at least one monomer (a2) from the group of unsaturated hydrophobically modified monomers.

Preferred copolymers a) are based on (at least one monomer a1) from the group of acrylic acid, methacrylic acid, $C_1$-$C_6$ alkyl acrylic acid ester, $C_1$-$C_6$ alkyl methacrylic acid ester. The acrylic acid esters and methacrylic acid esters are preferably esters of the respective acids with non-tertiary alkyl alcohols having alkyl radicals of from about 1 to about 12 carbon atoms, in particular from about 2 to about 4 carbon atoms. Examples of suitable monomers would be ethyl acrylate, ethyl methacrylate, propyl acrylate, propyl methacrylate, n-butyl acrylate, n-butyl methacrylate, isobutyl acrylate, 2-methylbutyl acrylate, 2-ethylhexyl acrylate, n-octyl acrylate, isooctyl acrylate, isooctyl methacrylate, isononyl acrylate and isodecyl acrylate.

The group of hydrophobically modified monomers (a2) denotes monomers which have a hydrophobic substructure. Preferred monomers (a2) can in turn be traced back to the two following structural units:
   an unsaturated acid, preferably acrylic acid, methacrylic acid or itaconic acid;
   a $C_{8-40}$ alkyl chain, preferably a $C_{10-30}$ alkyl chain, These two partial structures may optionally be supplemented by a third structural unit from the group of the polyoxyalkylene groups, preferably the polyethylene glycol groups, the polypropylene glycol groups or the polyethylene glycol/polypropylene glycol groups.

$C_{10-30}$ alkyl acrylates, $C_{10-30}$ alkyl PEG acrylates, $C_{10-30}$ alkyl PEG methacrylates or $C_{10-30}$ alkyl PEG itaconates are used, for example, as monomer (a2). Preferred monomers (a2) are selected from the $C_{10-30}$ alkyl acrylates, $C_{10-30}$ alkyl PEG 20-25 acrylates, $C_{10-30}$ alkyl PEG 20-25 methacrylates or $C_{10-30}$ alkyl PEG 20-25 itaconates. Particularly preferred monomers (a2) are selected from the group of $C_{10-30}$ alkyl methacrylates.

Particular preference is given to copolymers a) that are obtained by conversion of
   at least one monomer (a1) from the group of acrylic acid, methacrylic acid, $C_1$-$C_6$ alkyl acrylic acid ester, $C_1$-$C_6$ alkyl methacrylic acid ester, with
   at least one monomer (a2) from the group of $C_{10-30}$ alkyl acrylates, $C_{10-30}$ alkyl methacrylates, $C_{10-30}$ alkyl PEG acrylates, $C_{10-30}$ alkyl PEG methacrylates or $C_{10-30}$ alkyl PEG itaconates.

Very particular preference is given to copolymers a) that are obtained by conversion of
   at least one monomer (a1) from the group of acrylic acid, methacrylic acid, with
   at least one monomer (a2) from the group of $C_{10-30}$ alkyl methacrylates.

In summary, preferred cosmetic agents as contemplated herein are exemplified in that the copolymer a) is selected from the group of compounds with the INCI names Acrylates/$C_{10-30}$-Alkyl Methacrylate Copolymer, Acrylates/Steareth-20 Methacrylate Copolymer, Acrylates/Beheneth-25 Methacrylate Copolymer, Acrylates/Steareth-20 Itaconate Copolymer, Acrylates/Ceteth-20 Itaconate Copolymer, Acrylates/Palmeth-25 Acrylate Copolymer, Acrylates/Aminoacrylates/$C_{10-30}$ Alkyl PEG-20 Itaconat Copolymer. Corresponding polymers are available, for example, under the trade names Luvigel® FIT, Aculyn® 22, Aculyn® 28, Structure® 2001, Structure® 3001, Synthalen® W2000 and Structure® Plus. The copolymer a) is selected with particular preference from the group of compounds having the INCI name Acrylates/$C_{10-30}$-Alkyl Methacrylate Copolymer.

The proportion by weight of the copolymer a) in the total weight of the composition is preferably from about 0.1 to about 15% by weight, more preferably from about 0.2 to about 10% by weight and in particular from about 0.5 to about 7.0% by weight.

A second essential component of the cosmetic composition is the copolymer b) which can be traced back to the monomers i) styrene and ii) acrylic acid and/or methacrylic acid and optionally further monomers.

Preferred copolymers b) preferably includes at least about 90% by weight, preferably at least about 95% by weight and in particular at least about 97% by weight, of the monomers styrene and acrylic acid and/or methacrylic acid. Particularly preferred copolymers b) were obtained exclusively from the monomers styrene and acrylic acid and/or methacrylic acid.

The cosmetic agents of a further preferred embodiment are exemplified in that the at least one copolymer b) based on its total weight of at least about 90% by weight, preferably at least about 95% by weight and in particular at least about 97% by weight of the monomers
   styrene
   acrylic acid and/or methacrylic acid
   acrylic acid esters and/or methacrylic acid esters.

The copolymers b) described above, for example, are marketed under the name Acudyne® Shine (INCI name: Styrene/Acrylates Copolymer; CAS number 9010-92-8) from Dow Chemicals.

The proportion by weight of the copolymer b) in the total weight of the composition is preferably from about 0.1 to about 10% by weight, more preferably from about 0.2 to about 8.0% by weight and in particular from about 0.5 to about 7.0% by weight.

The copolymers a) and b) are preferably used in the cosmetic composition in partially neutralized or neutralized form. At least one alkanolamine is preferably used for neutralization. The alkanolamines which can be used as alkalizing agents as contemplated herein are preferably selected from primary amines having a $C_2$-$C_6$ alkyl basic body which carries at least one hydroxyl group. Particularly preferred alkanolamines are selected from the group formed from 2-aminoethan-1-ol (monoethanolamine), tris (2-hydroxyethyl) amine (triethanolamine), 3-aminopropan-1-ol, 4-aminobutane-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Very particularly preferred alkanolamines as contemplated herein are selected from the group including of 2-aminoethane-1-ol, 2-amino-2-methylpropan-1-ol and 2-amino-2-methylpropane-1,3-diol. 2-amino-2-methylpropanol has proven to be a particularly suitable neutralizing agent. Cosmetic compositions preferred as contemplated herein contain at least one alkanolamine, preferably 2-amino-2-methylpropanol. The 2-amino-2-methylpropanol is preferably used in the composition as contemplated herein in an amount which does not exceed the amount required to neutralize the copolymers a) and b). The amounts of 2-amino-2-methylpropanol used in the composition as contemplated herein are preferably from about 80 to about 100%, particularly preferably from about 90 to about 100% and in particular from about 95 to about 100% of the amount required for complete neutralization of the copolymers a) and b). Very particular preference is given to proportions by weight of the aminoalcohol, preferably of 2-amino-2-methylpropanol, in the total weight of the cosmetic composition from about 0.05 to about 2.0% by weight, preferably from about 0.1 to about 1.0% by weight, and in particular from about 0.1 to about 0.5% by weight.

Preferably, the cosmetic composition of the present disclosure contains one or more other polymers that are different from the copolymers a) and b), for example, supporting the thickening agents or the gel formation or the film formation. Examples are cationic, anionic, nonionic or amphoteric polymers.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, amino ethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, *bacillus*/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, poly ethylacrylate, polyethylene terephthalate, polymethacryloyl ethyl betaine, polypentaerythrityl terephthalate, polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polyquaternium-68, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVPNA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate and styrene/VP copolymer.

The further component acting as gel formatting agent is preferably a homopolyacrylic acid (INCI: Carbomer), which is commercially available, for example, under the name Carbopol® in different versions. The Carbomer is preferably present in an amount of from about 0.02 to about 3% by weight, preferably from about 0.05 to about 1.5% by weight, and more preferably from about 0.2 to about 0.8% by weight, based on the total weight of the cosmetic composition.

In order to further increase their cosmetic effect, preferred compositions contain, in addition to the copolymers a) and b) and an optionally added thickening agent or gel formation agent, further contain a film-forming polymer c) different from these ingredients, in particular an anionic or nonionic polymer c).

Examples of nonionic polymers are:
vinylpyrrolidone/vinyl ester copolymers, such as those sold under the trademark Luviskol (BASF). Luviskol VA 64 and Luviskol VA 73, in each case vinylpyrrolidone/vinyl acetate copolymers, are preferred nonionic polymers.
cellulose ethers, such as hydroxypropylcellulose, hydroxyethylcellulose and methylhydroxypropylcellulose, as sold, for example, under the trademarks Culminal and Benecel (AQUALON).
shellac.
polyvinylpyrrolidone, as sold for example under the name Luviskol (BASF).
siloxanes. These siloxanes can be both water-soluble and water-insoluble. Both volatile and nonvolatile siloxanes are suitable, wherein nonvolatile siloxanes are understood to mean those compounds whose boiling point is above about 200° C. under normal pressure. Preferred siloxanes are polydialkylsiloxanes, such as, for example, polydimethylsiloxane, polyalkylarylsiloxanes, such as, for example, polyphenylmethylsiloxane, ethoxylated polydialkylsiloxanes and polydialkylsiloxanes which contain amine and/or hydroxyl groups.
glycosidically substituted silicones.

Based on their cosmetic action in combination with the copolymers a) and b), film-forming polymers preferably used as contemplated herein are the polyvinylpyrrolidones (INCI name: PVP) and the vinylpyrrolidone/vinyl acetate copolymers (INCI name VP/VA Copolymer). By adding film-forming polymers, in particular the abovementioned polyvinylpyrrolidones and vinylpyrrolidone/vinyl acetate copolymers, the holding properties but also the application properties of the cosmetic compositions are noticeably influenced in an advantageous manner. The proportion by weight of these polymers is preferably limited to amounts between from about 1.0 and about 10% by weight. Preferred cosmetic compositions as contemplated herein are therefore exemplified in that, based on their total weight, they furthermore contain from about 1.0 to about 10% by weight of polyvinylpyrrolidone and/or vinylpyrrolidone/vinyl acetate copolymer, preferably polyvinylpyrrolidone. Particularly preferred cosmetic compositions have a proportion by weight of the polyvinylpyrrolidone and/or vinylpyrrolidone/vinyl acetate copolymer c) in the total weight of the cosmetic composition from about 2.0 to about 8.5% by weight, preferably from about 3.0 to about 7.0% by weight.

The cosmetic composition of the present disclosure may contain other conventional substances of styling products. Other suitable auxiliaries and additives are, in particular, additional care substances.

As a care substance, the agent may contain, for example, at least one protein hydrolyzate and/or one of its derivatives. Protein hydrolyzates are product mixtures that are obtained by acid, alkaline or enzymatically catalyzed degradation of proteins. As contemplated herein, the term protein hydrolyzates is also understood to mean total hydrolyzates and individual amino acids and their derivatives and mixtures of different amino acids. The molecular weight of the usable protein hydrolyzates as contemplated herein is between about 75, the molecular weight for glycine, and about 200,000, preferably the molecular weight is from about 75 to about 50,000 and very particularly preferably from about 75 to about 20,000 daltons.

As a care substance, the agent as contemplated herein may further contain at least one vitamin, a provitamin, a vitamin precursor and/or one of their derivatives. As contemplated herein, such vitamins, provitamins and vitamin precursors which are usually assigned to the groups A, B, C, E, F and H are preferred.

As with the addition of glycerol and/or propylene glycol, the addition of panthenol increases the flexibility of the polymer film formed using the composition according to the present disclosure.

The compositions as contemplated herein may further contain at least one plant extract, but also mono- or oligosaccharides and/or lipids as a care substance.

Furthermore, oil bodies are suitable as a care substance. The natural and synthetic cosmetic oil bodies include, for example, vegetable oils, liquid paraffin oils, isoparaffin oils and synthetic hydrocarbons and di-n-alkyl ethers having a total of between from about 12 and about 36 carbon atoms, in particular from about 12 to about 24 carbon atoms. Preferred cosmetic agents as contemplated herein contain at least one oil body, preferably at least one oil body from the group of silicone oils. The group of silicone oils includes in particular the dimethicones, to which the cyclomethicones are also to be counted, the amino-functional silicones and the dimethiconols. The dimethicones may be both linear and branched and cyclic or cyclic and branched. Suitable silicone oils or silicone gums are, in particular, dialkyl and alkylaryl siloxanes, for example dimethylpolysiloxane and methylphenylpolysiloxane, and also their alkoxylated, quaternized or else anionic derivatives. Preference is given to cyclic and linear polydialkylsiloxanes, their alkoxylated and/or aminated derivatives, dihydroxypolydimethylsiloxanes and polyphenylalkylsiloxanes.

Ester oils, that is, esters of 6-C30 fatty acids with C2-C30 fatty alcohols, preferably monoester of fatty acids with alcohols having from about 2 to about 24 carbon atoms such as isopropyl myristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, cocofatty alcohol caprate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoate (Cetiol® SN), decyl oleate (Cetiol® V) are more preferred caring oil bodies.

Also suitable as care products are dicarboxylic acid esters, symmetrical, asymmetrical or cyclic esters of carbonic acid with fatty alcohols, triflic acid esters of saturated and/or unsaturated linear and/or branched fatty acids with glycerol or fatty acid partial glycerides, which are understood to mean monoglycerides, diglycerides and their technical mixtures.

Furthermore, emulsifiers or surface-active substances are preferably present in the composition as contemplated herein. Preferred are PEG derivatives of hydrogenated castor oil which are available, for example, under the name PEG Hydrogenated Castor Oil, e.g., PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. Preferred as contemplated herein is the use of PEG-40 Hydrogenated Castor Oil. These are preferably present in an amount from about 0.05 to about 1.5% by weight, more preferably from about 0.1 to about 1.0% by weight, also preferably from about 0.2 to about 0.8% by weight or from about 0.3 to about 0.6% by weight. By adding the surface-active substances, in particular the abovementioned PEG derivatives of hydrogenated castor oil, in addition to the processibility, the ability of the cosmetic compositions to be washed out is improved in particular.

The cosmetic compositions as contemplated herein contain the ingredients or active ingredients in a cosmetically tolerable carrier.

Preferred cosmetically tolerable carriers are aqueous, alcoholic or aqueous-alcoholic media having preferably at least about 10% by weight of water, calculated on the total weight of the agent. The cosmetic carrier as contemplated herein particularly preferably contains water, in particular in an amount such that the cosmetic composition, based on its total weight, contains at least about 20% by weight, in particular at least about 40.0% by weight, most preferably at least about 70% by weight of water and ethanol. Very particularly preferred cosmetic compositions have, based on their total weight, a water and ethanol content from about 50 to about 95% by weight, preferably from about 60 to about 90% by weight and in particular from about 65 to about 85% by weight.

As further alcohols, it is possible in particular to include the lower alcohols having from about 1 to about 4 carbon atoms, typically used for cosmetic purposes, such as, for example, isopropanol.

Examples of water-soluble solvents as cosolvent are glycerol and/or ethylene glycol and/or 1,2-propylene glycol in an amount of from about 0 to about 30% by weight based on the total agent.

The composition of some preferred cosmetic agents can be found in the following tables (in % by weight based on the total weight of the cosmetic agent, unless stated otherwise).

|  | Formula 1 | Formula 2 | Formula 3 | Formula 4 | Formula 5 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Misc | ad 100 | ad 100 | ad 100 | ad 100 | ad 100 |

|  | Formula 1a | Formula 2a | Formula 3a | Formula 4a | Formula 5a |
|---|---|---|---|---|---|
| Acrylates/ $C_{10-30}$ Alkyl Methacrylate Copolymer | 0.1 to 15 | 0.2 to 10 | 0.2 to 10 | 0.5 to 7.0 | 0.5 to 7.0 |
| Styrene/ Acrylates Copolymer | 0.1 to 10 | 0.1 to 10 | 0.2 to 8.0 | 0.2 to 8.0 | 0.5 to 7.0 |
| Misc | ad 100 | ad 100 | ad 100 | ad 100 | ad 100 |

|  | Formula 1b | Formula 2b | Formula 3b | Formula 4b | Formula 5b |
|---|---|---|---|---|---|
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Misc | ad 100 | ad 100 | ad 100 | ad 100 | ad 100 |

|  | Formula 6 | Formula 7 | Formula 8 | Formula 9 | Formula 10 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 6a | Formula 7a | Formula 8a | Formula 9a | Formula 10a |
|---|---|---|---|---|---|
| Acrylates/ $C_{10-30}$ Alkyl Methacrylate Copolymer | 0.1 to 10 | 0.1 to 10 | 0.2 to 8.0 | 0.2 to 8.0 | 0.5 to 7.0 |
| Styrene/ Acrylates Copolymer | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 6b | Formula 7b | Formula 8b | Formula 9b | Formula 10b |
|---|---|---|---|---|---|
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 11 | Formula 12 | Formula 13 | Formula 14 | Formula 15 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 11a | Formula 12a | Formula 13a | Formula 14a | Formula 15a |
|---|---|---|---|---|---|
| Acrylates/ $C_{10-30}$ Alkyl Methacrylate Copolymer | 0.1 to 15 | 0.2 to 10 | 0.2 to 10 | 0.5 to 7.0 | 0.5 to 7.0 |
| Styrene/ Acrylates Copolymer | 0.1 to 10 | 0.1 to 10 | 0.2 to 8.0 | 0.2 to 8.0 | 0.5 to 7.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 11b | Formula 12b | Formula 13b | Formula 14b | Formula 15b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | ad 100 | ad 100 | ad 100 | ad 100 | ad 100 |

|  | Formula 16 | Formula 17 | Formula 18 | Formula 19 | Formula 20 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Misc | ad 100 | ad 100 | ad 100 | ad 100 | ad 100 |

|  | Formula 16a | Formula 17a | Formula 18a | Formula 19a | Formula 20a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Misc | ad 100 | ad 100 | ad 100 | ad 100 | ad 100 |

|  | Formula 16b | Formula 17b | Formula 18b | Formula 19b | Formula 20b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Misc | ad 100 | ad 100 | ad 100 | ad 100 | ad 100 |

|  | Formula 21 | Formula 22 | Formula 23 | Formula 24 | Formula 25 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | ad 100 | ad 100 | ad 100 | ad 100 | ad 100 |

|  | Formula 21a | Formula 22a | Formula 23a | Formula 24a | Formula 25a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | ad 100 | ad 100 | ad 100 | ad 100 | ad 100 |

|  | Formula 21b | Formula 22b | Formula 23b | Formula 24b | Formula 25b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | ad 100 | ad 100 | ad 100 | ad 100 | ad 100 |

|  | Formula 26 | Formula 27 | Formula 28 | Formula 29 | Formula 30 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 26a | Formula 27a | Formula 28a | Formula 29a | Formula 30a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 26b | Formula 27b | Formula 28b | Formula 29b | Formula 30b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 31 | Formula 32 | Formula 33 | Formula 34 | Formula 35 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 31a | Formula 32a | Formula 33a | Formula 34a | Formula 35a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 31b | Formula 32b | Formula 33b | Formula 34b | Formula 35b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 36 | Formula 37 | Formula 38 | Formula 39 | Formula 40 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 36a | Formula 37a | Formula 38a | Formula 39a | Formula 40a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 36b | Formula 37b | Formula 38b | Formula 39b | Formula 40b |
|---|---|---|---|---|---|
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 41 | Formula 42 | Formula 43 | Formula 44 | Formula 45 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Water/ethanol | 50 to 95 | 50 to 95 | 60 to 90 | 60 to 90 | 65 to 85 |
| Misc | ad 100 | ad 100 | ad 100 | ad 100 | ad 100 |

25

|  | Formula 41a | Formula 42a | Formula 43a | Formula 44a | Formula 45a |
|---|---|---|---|---|---|
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 41b | Formula 42b | Formula 43b | Formula 44b | Formula 45b |
|---|---|---|---|---|---|
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Carbomer | 0.02 to 3.0 | 0.05 to 2.0 | 0.05 to 1.5 | 0.2 to 1.5 | 0.2 to 0.8 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 46 | Formula 47 | Formula 48 | Formula 49 | Formula 50 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 46a | Formula 47a | Formula 48a | Formula 49a | Formula 50a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 46b | Formula 47b | Formula 48b | Formula 49b | Formula 50b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 51 | Formula 52 | Formula 53 | Formula 54 | Formula 55 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 51a | Formula 52a | Formula 53a | Formula 54a | Formula 55a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 51b | Formula 52b | Formula 53b | Formula 54b | Formula 55b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 56 | Formula 57 | Formula 58 | Formula 59 | Formula 60 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 56a | Formula 57a | Formula 58a | Formula 59a | Formula 60a |
| --- | --- | --- | --- | --- | --- |
| Acrylates/$C_{10-30}$ Alkyl Methacrylate Copolymer | 0.1 to 15 | 0.2 to 10 | 0.2 to 10 | 0.5 to 7.0 | 0.5 to 7.0 |
| Styrene/Acrylates Copolymer | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

|  | Formula 56b | Formula 57b | Formula 58b | Formula 59b | Formula 60b |
| --- | --- | --- | --- | --- | --- |
| Luvigel ® Fit Up (specified as solids content) | 0.1 to 15 | 0.2 to 10 | 0.2 to 10 | 0.5 to 7.0 | 0.5 to 7.0 |
| Acudyne ® Shine (specified as solids content) | 0.1 to 10 | 0.1 to 10 | 0.2 to 8.0 | 0.2 to 8.0 | 0.5 to 7.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water/ethanol | 50 to 95 | 50 to 95 | 60 to 90 | 60 to 90 | 65 to 85 |
| Misc | ad 100 | ad 100 | ad 100 | ad 100 | ad 100 |

As contemplated herein, "Misc" is understood to mean a cosmetic carrier, in particular (unless stated separately) water and optionally further customary constituents of styling products.

The cosmetic composition of the present disclosure may be formulated in the shapes customary for the temporary shaping of hair, e.g., as a hair gel, hair spray, hair mousse or hair wax. Preference is given to the preparation as a hair gel.

Both hair mousses and hair sprays require the presence of foaming agents. As contemplated herein, however, preferably no or only small amounts of hydrocarbons should be used for this purpose. Propane, propane/butane mixtures and dimethyl ether are particularly suitable foaming agents as contemplated herein.

The present disclosure also relates to the use of cosmetic compositions as contemplated herein for the temporary shaping of keratinic fibers, in particular of human hair, and a method for the temporary deformation of keratinic fibers, in particular human hair, in which the keratinic fibers are acted upon by a cosmetic composition as contemplated herein and temporarily fixed in their shape.

A further subject of this patent application is the use of a cosmetic composition as contemplated herein for improving the holding of temporarily deformed keratinic fibers.

A final subject of this patent application is the use of a cosmetic composition as contemplated herein for improving the moisture resistance of temporarily deformed keratinic fibers.

EXAMPLES

The following hair gels were produced:

| Component/raw material | INCI name or chemical name | V1 | V2 | E1 |
|---|---|---|---|---|
| Luvigel ® Fit UP[1] | Acrylates (C10-30) Alkyl Methacrylate Copolymer | 3.33 | — | 1.66 |
| Acudyne ® Shine[2] | Styrene/Acrylates Copolymer | — | 2.5 | 1.25 |
| AMP-ULTRA PC 2000 | Aminomethyl propanol | 0.45 | 0.27 | 0.36 |
| Water | | 96.22 | — | 48.11 |
| Ethanol | | — | 97.23 | 48.62 |
| Total | | 100 | 100 | 100 |

[1]30% by weight of active substance in water
[2]40% by weight of active substance in water The quantities in the table are specified in % by weight of the respective raw material, based on the total composition. The polymer content in each of the compositions V1, V2 and E1 was 1.0% by weight.

For the styling agents obtained, the moisture resistance was determined on purified Kerling hair strands by employing an HHCR test (High Humidity Curl Retention Test: 6 h) (mean value for determining each 5 hair strands):

| | V1 | V2 | E1 |
|---|---|---|---|
| HHCR | 62% | 33% | 68% |

The polymer combination E1 as contemplated herein therefore showed a clearly superadditive, synergistic effect with respect to the moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for the temporary shaping of keratinic fibers, comprising:
   a) at least one non-crosslinked, hydrophobically modified (meth)acrylic acid copolymer, wherein the at least one non-crosslinked, hydrophobically modified (meth) acrylic acid copolymer a) has the INCI name Acrylates/$C_{10-30}$ Alkyl Methacrylate Copolymer, and
   b) at least one copolymer comprising at least in part monomer units including:
   styrene, and
   acrylic acid and/or methacrylic acid, wherein the at least one copolymer b) has the INCI name Styrene/Acrylates Copolymer; and
   wherein a proportion by weight of the copolymer a) in the total weight of the composition is about 0.5% by weight, and wherein the proportion by weight of the copolymer b) in the total weight of the composition is about 0.5% by weight.

2. The cosmetic composition according to claim 1, wherein the cosmetic composition is selected from the group of a hair gel, a hair spray, a hair mousse, or a hair wax.

3. The cosmetic composition according to claim 2, wherein the hair gel, the hair spray, the hair mousse, and the hair wax are formulated for the temporary deformation of hair.

4. The cosmetic composition according to claim 1, further comprising:
   c) polyvinylpyrrolidone and/or vinylpyrrolidone/vinyl acetate copolymer.

5. The cosmetic composition according to claim 4, wherein the proportion by weight of the polyvinylpyrrolidone and/or vinylpyrrolidone/vinyl acetate copolymer c) in the total weight of the cosmetic composition is from about 0.1 to about 10% by weight.

6. The cosmetic composition according to claim 4, wherein the proportion by weight of the polyvinylpyrrolidone and/or vinylpyrrolidone/vinyl acetate copolymer c) in the total weight of the cosmetic composition is from about 2.0 to about 8.5% by weight.

7. The cosmetic composition according to claim 4, wherein the proportion by weight of the polyvinylpyrrolidone and/or vinylpyrrolidone/vinyl acetate copolymer c) in the total weight of the cosmetic composition is from about 3.0 to 7.0% by weight.

8. The cosmetic composition according to claim 1, wherein the composition comprises, based on its total weight, at least about 20% by weight of water.

9. The cosmetic composition according to claim 1, further comprising:
   c) polyvinylpyrrolidone.

10. The cosmetic composition according to claim 1, wherein the composition comprises, based on its total weight, at least about 40% by weight of water.

11. The cosmetic composition according to claim 1, wherein the composition comprises, based on its total weight, at least about 70% by weight of water.

12. A method comprising using a cosmetic composition according to claim 1 for the temporary deformation of keratin-containing fibers.

13. A method for the temporary deformation of keratin-containing fibers, the method comprising acting upon the keratinic fibers by a cosmetic composition according to claim 1 while the keratinic fibers are temporarily fixed in a shape.

* * * * *